(12) United States Patent
Wang et al.

(10) Patent No.: US 8,765,056 B2
(45) Date of Patent: Jul. 1, 2014

(54) METHOD FOR DETECTING OPTICAL SIGNALS, MICROFLUIDIC MIXING CHIP HAVING LIGHT EMITTING COMPOUND AND SYSTEM THEREOF

(75) Inventors: Shau-Chun Wang, Chiayi (TW); Pei-Ching Hung, Pingtung (TW); Chun-Yi Yeh, Magong (TW)

(73) Assignee: National Chung Cheng University, Chia-Yi (TW)

( * ) Notice: Subject to any disclaimer, the term of this patent is extended or adjusted under 35 U.S.C. 154(b) by 507 days.

(21) Appl. No.: 12/959,545

(22) Filed: Dec. 3, 2010

(65) Prior Publication Data
US 2011/0294225 A1 Dec. 1, 2011

(30) Foreign Application Priority Data
Jun. 1, 2010 (TW) .............................. 99117675 A

(51) Int. Cl.
*G01N 21/76* (2006.01)
*G01N 21/68* (2006.01)
*G01N 21/03* (2006.01)

(52) U.S. Cl.
CPC ............... *G01N 21/76* (2013.01); *G01N 21/68* (2013.01); *G01N 21/763* (2013.01); *G01N 2021/0325* (2013.01); *G01N 2021/0346* (2013.01)
USPC ........................... 422/52; 422/82.05; 436/172

(58) Field of Classification Search
None
See application file for complete search history.

(56) References Cited

PUBLICATIONS

Kiba, N., et al. Flow-through micro sensor using immobilized peroxidase with chemiluminometric FIA system for determining hydrogen peroxide, 2003, Analytical Sciences, vol. 19, pp. 823-827.*
Lim, C. Y., et al., Mixing enhancement in microfluidic channel with a construction under periodic electro-osmotic flow, 2010, Biomicrofluidics, vol. 4, pp. 014101-1 to 014101-18.*
Wang, S. et al., AC elecro-osmotic mixing induced by non-contact external electrodes, 2006, Biosensors and Bioelectronics, vol. 22, pp. 563-567.*

\* cited by examiner

*Primary Examiner* — Robert Xu
(74) *Attorney, Agent, or Firm* — Harness, Dickey & Pierce, PLC

(57) ABSTRACT

A method for detecting optical signals, a microfluidic mixing chip having light emitting compound and a system thereof are provided. The microfluidic mixing system comprises the microfluidic mixing chip, an electrode pairs and a power supplier. The microfluidic mixing chip comprises a first side cavity, a second side cavity and a mixing cavity. The mixing cavity is disposed between the first side cavity and the second side cavity. The mixing cavity further contains the light emitting compound, a catalyst and a redox reagent. The electrode pair is respectively disposed to the first side cavity and the second cavity. The power supplier supplies a power source with high frequency alternating current electric field. By utilizing the power source with alternating current electric field, the light emitting compound, the redox reagent and the catalyst are mixed in the mixing cavity to generate a chemiluminescence or bioluminescence optical signal to detect.

13 Claims, 8 Drawing Sheets

METHOD FOR DETECTING OPTICAL SIGNALS, MICROFLUIDIC MIXING CHIP HAVING LIGHT EMITTING COMPOUND AND SYSTEM THEREOF

BACKGROUND OF THE INVENTION

1. Field of the Invention

The present invention relates to a method for detecting optical signals, microfluidic mixing chip and a system thereof, and more particularly to a method for detecting a chemiluminescence optical signal or a bioluminescence optical signal, and a microfluidic mixing chip having light emitting compound and a system thereof.

2. Description of the Related Art

After many analysis techniques have been developed and matured since 1990, system miniature becomes an important goal exerted by scientists. When microelectromechanical process technique is simultaneously developed, the difficulty of manufacturing the miniature experimental platform is reduced. The multiplexing experimental platform combined with injection, reaction, isolation, and analysis can be disposed on the same micro-chip as a microfluidic chip.

The microfluidic system provides many advantages after system is minimized such as reduced sample demands, shortened analysis time, high sensitivity, decreased manufacturing and operating costs, etc. In addition, since the minimized system can be easily carried, the system operation is not so hard.

Although the microfluidic system has been widely applied in many fields and the system also shows excellent achievements, the problems on the system need to be overcome. In some analysis processes, reagents with low diffusion coefficient need to be performed with rapid mixing reaction such as DNA (deoxyribonucleic acid) hybridization. If the mixing time required by such reaction is equal to or larger than the time required by reaction, the rapid and uniform mixing process is quite important.

SUMMARY OF THE INVENTION

In view of the shortcomings of the prior art, the inventor(s) of the present invention based on years of experience in the related industry to conduct extensive researches and experiments, and finally developed a method for detecting optical signals, a microfluidic mixing chip having light emitting compound and its system capable of continuously detecting chemiluminescence optical signals or bioluminescence optical signals in short time.

Therefore, it is an objective of the present invention to overcome the aforementioned shortcoming and deficiency of the prior art by providing a method for detecting optical signals, a microfluidic mixing chip having light emitting compound and its system.

To achieve the foregoing objective, the microfluidic mixing chip having light emitting compound of the invention comprises a first side cavity, a second side cavity and a mixing cavity. The mixing cavity is disposed between the first side cavity and the second side cavity and is connected to one another by microchannels. The mixing cavity contains the light emitting compound as well as a redox reagent or a catalyst. A pair of electrodes is respectively disposed to a first side cavity and a second side cavity to provide a power source with high frequency alternating current electric field. When a redox reagent or a catalyst has been added, the light emitting compound, the redox reagent and the catalyst are mixed in the mixing cavity to generate the chemiluminescence optical signals or the bioluminescence optical signals by utilizing the power source with high frequency alternating current electric field.

To achieve the foregoing objective, the method for detecting optical signals of the invention is suitable for the microfluidic mixing chip. The microfluidic mixing chip comprises a first side cavity, a second side cavity and a mixing cavity. The method for detecting optical signals comprises the following steps. Firstly, the mixing cavity is disposed between the first side cavity and the second side cavity and connected to one another through microchannels. Secondly, a light emitting compound as well as a redox reagent or a catalyst are placed into the mixing cavity. Next, electrodes are respectively disposed to the first side cavity and the second side cavity to provide a power source with high frequency alternating current electric field. When a redox reagent or a catalyst has been added, the light emitting compound, the redox reagent and the catalyst are mixed in the mixing cavity to generate chemiluminescence optical signals or bioluminescence optical signals by utilizing the power source with high frequency alternating current electric field. Finally, the chemiluminescence optical signals or the bioluminescence optical signals are detected by a photon sensitive detector.

To achieve the foregoing objective, the microfluidic mixing system having light emitting compound of the invention comprises a microfluidic mixing chip, an electrode pair and a power supplier. The microfluidic mixing chip comprises a first side cavity, a second side cavity and a mixing cavity. The mixing cavity is disposed between the first side cavity and the second side cavity and connected to one another through microchannels. The mixing cavity contains the light emitting compound and a redox reagent. A pair of electrodes is respectively disposed to the first side cavity and the second side cavity. The power supplier supplies a power source with high frequency alternating current electric field. The light emitting compound, the redox reagent and a catalyst are mixed in the mixing cavity to generate chemiluminescence optical signals or bioluminescence optical signals by utilizing the power source with high frequency alternating current electric field.

The method for detecting optical signals, the microfluidic mixing chip having the light emitting compound and its system of the invention have one or more advantages.

(1) The invention could continuously detect emitted light generated by a chemiluminescence reaction in the presence of catalyst such as ferric ions in short time and enhance the distribution reproducibility of the chemiluminescence optical signals by incorporating a photon sensitive detector, such as a charge coupled device (CCD), a photo multiplier tube (PMT).

(2) The invention could detect the bioluminescence optical signals by utilizing a charge-coupled device (CCD).

(3) The invention induces electric charges of sharp-cornered intersection angles within the channel to generate electroosmotic flow through alternating current. With the electroosmotic flow, the sample can be mixed at high efficiency in short time so that time of mixing the sample can be shortened.

DETAILED DESCRIPTION OF THE PREFERRED EMBODIMENTS

The foregoing and other technical characteristics of the present invention will become apparent with the detailed description of the preferred embodiments and the illustration of the related drawings.

Figure 1:
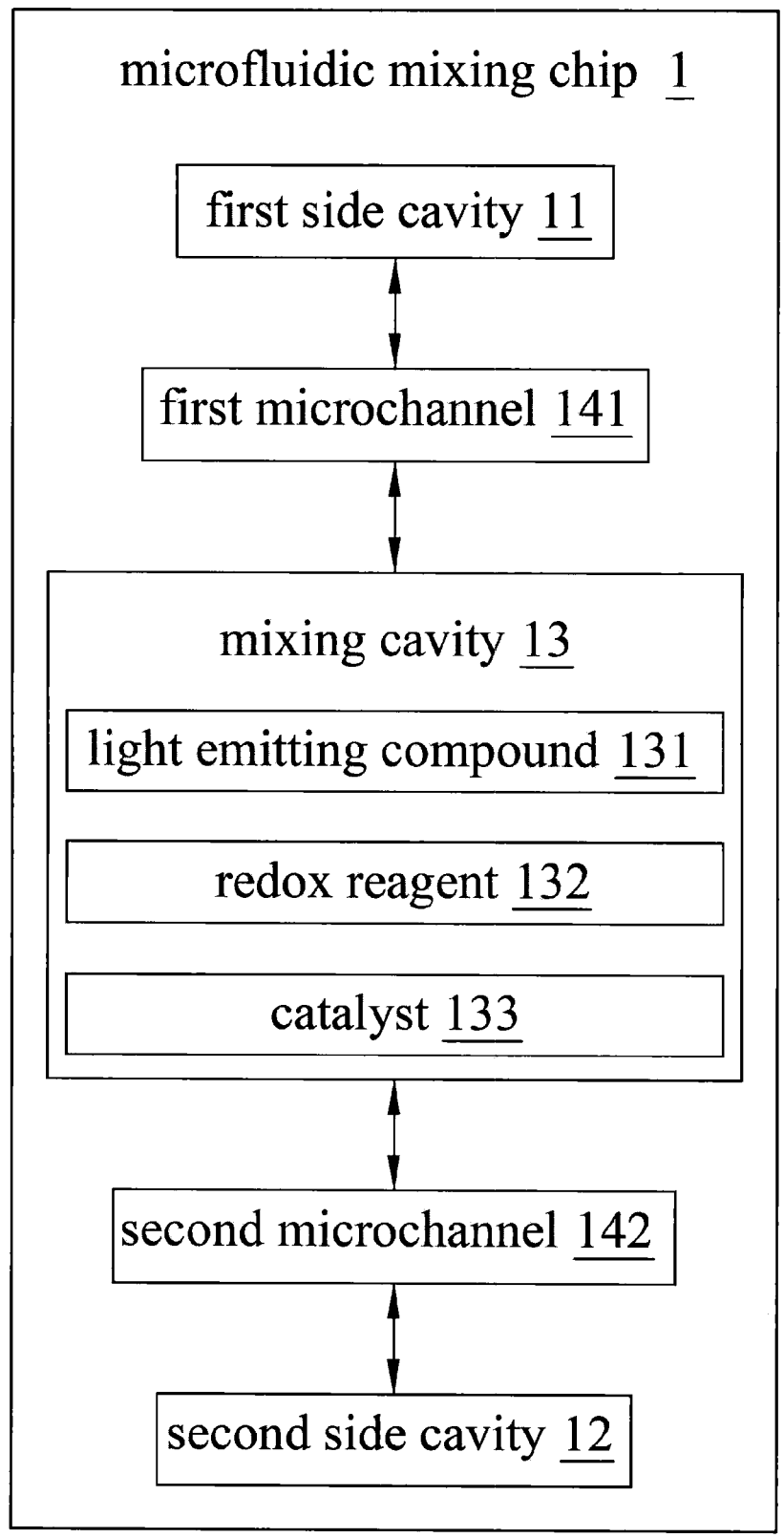
FIG. 1 is a schematic diagram of a microfluidic mixing chip having light emitting compound according to the present invention.

With reference to FIG. 1 for a schematic diagram of a microfluidic mixing chip having light emitting compound in accordance with the present invention is depicted. As shown in the figure, the microfluidic mixing chip 1 comprises a first side cavity 11, a second side cavity 12 and a mixing cavity 13. The mixing cavity 13 is disposed between the first side cavity 11 and the second side cavity 12 and connected to one another through a first microchannel 141 and a second microchannel 142. The mixing cavity contains the light emitting compound 131 a redox reagent 132 and a catalyst 133. The light emitting compound can be lucigenin, luminol or lophine. A pair of electrodes is disposed to the first side cavity 11 and the second side cavity 12 to provide a power source with high frequency alternating current electric field. The light emitting compound 131, the redox reagent 132 and the catalyst 133 are mixed in the mixing cavity 13 to generate chemiluminescence (CL) optical signals or bioluminescence (BL) optical signals by utilizing the power source with high frequency alternating current electric field.

Chemiluminescence is defined that light emitting molecules irradiate and emit light (It can be at the scope of visible light or far infrared ray) through chemical reaction. When the energy generated by the chemical reaction is enough, electrons are induced to form excited state from ground state. When the electrons return to ground state from excited state, the irradiated light of the electrons is so called chemiluminescence. Bioluminescence is generated from biological bodies through chemical reaction and is a chemical light emitting. For instance, light generated by fireflies is the best example of bioluminescence.

In the luminol chemiluminescence system, the composition of luminol/hydrogen peroxide/catalyst/alkaline aqueous solution is adopted and most popular. The intensity of chemiluminescence is directly proportion to the concentrations of luminol, hydrogen peroxide and the catalyst. The measurement of chemiluminescence intensity can be taken as quantitative analysis for concentration. The types of the catalysts has included but not limited to transition metals (e.g. Fe(II), Fe(III), Co(II), Ni(II), Cu(II), etc) and their complex compound (e.g. $Fe(CN)_6^{3-}$, $Cu(NH_3)_6^{2+}$, etc) and peroxidase enzymes. Different catalysts may influence the generation of chemiluminescence of luminol. The redox reagent can be but not limited to hydrogen peroxide or oxygen.

Figure 2:
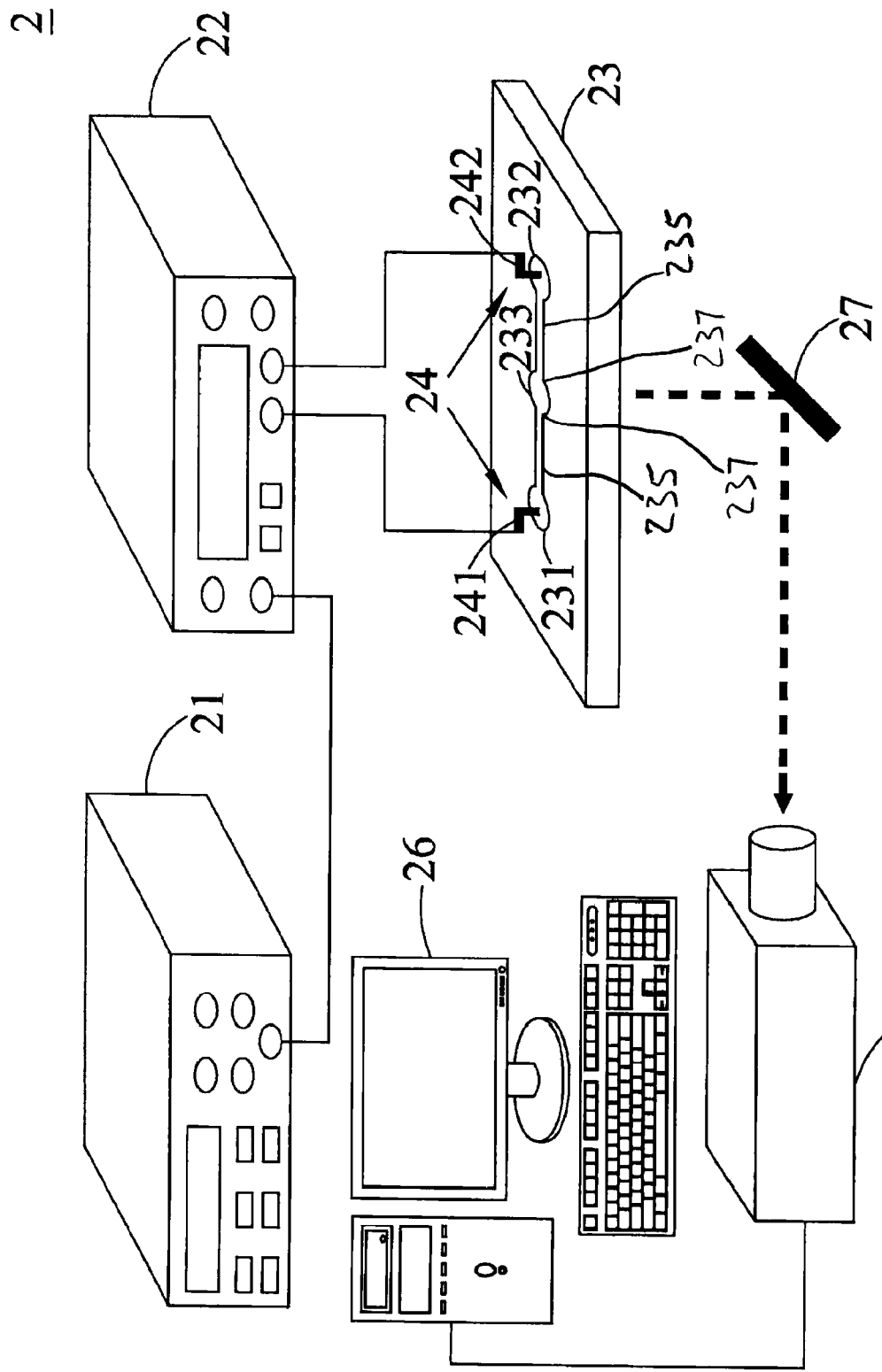
FIG. 2 is a schematic diagram of a microfluidic mixing system having light emitting compound according to the present invention.

With reference to FIG. 2 for a schematic diagram of a microfluidic mixing system having light emitting compound is depicted. As shown in the figure, the microfluidic mixing system 2 having light emitting compound comprises a power supplier 21, a voltage amplifier 22, a microfluidic mixing chip 23, an electrode pair 24, a photon sensitive detector 25 and a computer 26. The power supplier 21 can be a function generator. Since the voltage amplifier 22 is connected to the microfluidic mixing chip 23, a power source with high frequency alternating current electric field is supplied to the microfluidic mixing chip 23. The voltage amplifier 22 is provided for amplifying electric signals of the power source.

The electrode pair 24 can be a platinum electrode, wherein one of the electrodes is disposed to a first side cavity 231 while another electrode is disposed to a second side cavity 232.

When the power supplier 21 supplies the power source to the microfluidic mixing chip 23, the light emitting compound, a redox reagent and a catalyst in a mixing cavity 233 are mixed to further generate chemiluminescence (CL) optical signals or bioluminescence (BL) optical signals. As shown in FIG. 2, the mixing cavity 233 is connected to the first and second side cavities 231, 232 by microchannels 235. The mixing cavity 233 is joined to the microchannels 235 at sharp corners 237.

To allow the photon sensitive detector 25 receiving the chemiluminescence (CL) optical signals or the bioluminescence (BL) optical signals, the invention further comprises a focusing optics set 27 that is disposed between the microfluidic mixing chip 23 and the photon sensitive detector 25 to focus the chemiluminescence (CL) optical signals or the bioluminescence (BL) optical signals. The photon sensitive detector 25 can be a charge coupled device (CCD), a photo multiplier tube (PMT) or other types of photon sensitive detector.

The processor 26 is connected to the photon sensitive detector 25 to process the optical signals detected by the photon sensitive detector 25.

Figure 3:
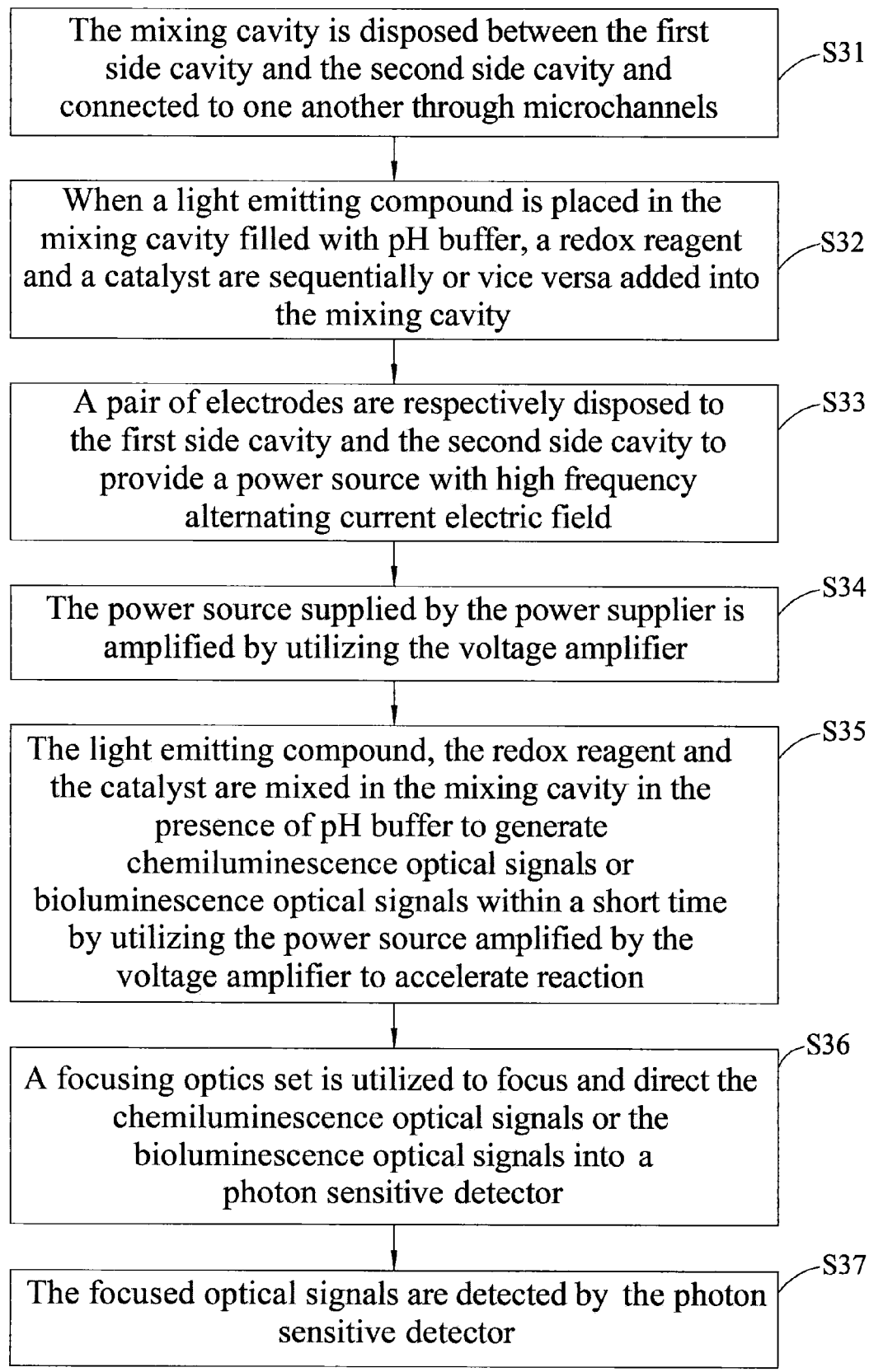
FIG. 3 is a flow chart of a method for detecting optical signals according to the present invention.

With reference to FIG. 3 for a flow chart of a method for detecting optical signals in accordance with the invention is depicted. The method is suitable for the microfluidic mixing chip. The microfluidic mixing chip comprises a first side cavity, a second side cavity and a mixing cavity. The method comprises the following steps: step S31: The mixing cavity is disposed between the first side cavity and the second side cavity and connected to one another through microchannels; step S32: When a light emitting compound is placed in the mixing cavity filled with pH buffer, a redox reagent and a catalyst are sequentially or vice versa added into the mixing cavity, and the light emitting compound can be lucigenin, luminol or lophine; step S33: A pair of electrodes are respectively disposed to the first side cavity and the second side cavity to provide a power source with high frequency alternating current electric field; step S34: The power source supplied by the power supplier is amplified by utilizing the voltage amplifier; step S35: The light emitting compound, the redox reagent and the catalyst are mixed in the mixing cavity in the presence of pH buffer to generate chemiluminescence optical signals or bioluminescence optical signals within a short time by utilizing the power source amplified by the voltage amplifier to accelerate reaction, and the catalyst can be potassium ferricyanide, and the pH buffer can be sodium hydroxide; step S36: A focusing optics set is utilized to focus and direct the chemiluminescence optical signals or the bioluminescence optical signals into a photon sensitive detector; step S37: The focused optical signals are detected by the photon sensitive detector, and the photon sensitive detector can be a CCD, a PMT, or other types of photon sensitive detector.

<A First Embodiment: Taking the CCD for Detection>

Figure 4A:
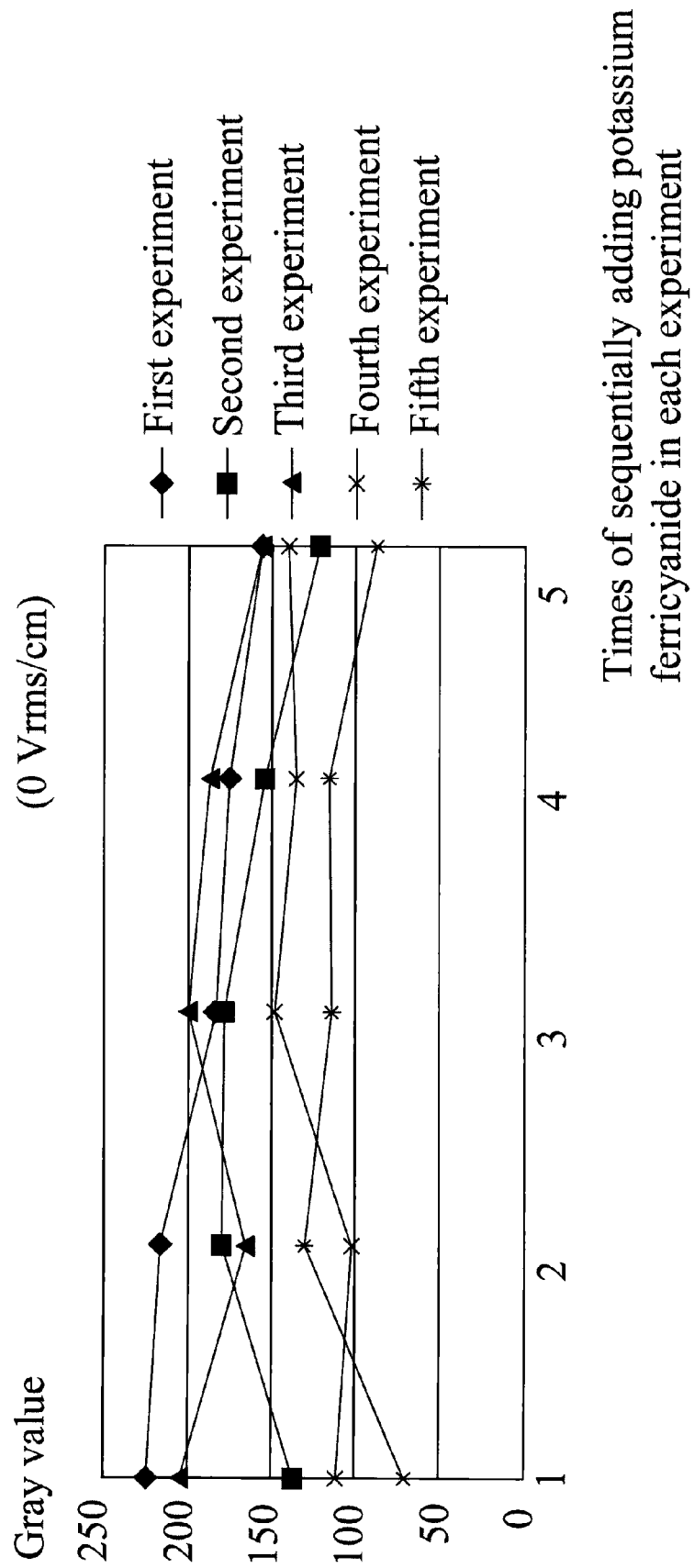
FIG. 4A is an illustration of chemilluminescence light reproducibility using a microfluidic mixing system without electric field according to a first embodiment of the present invention.
Figure 4B:
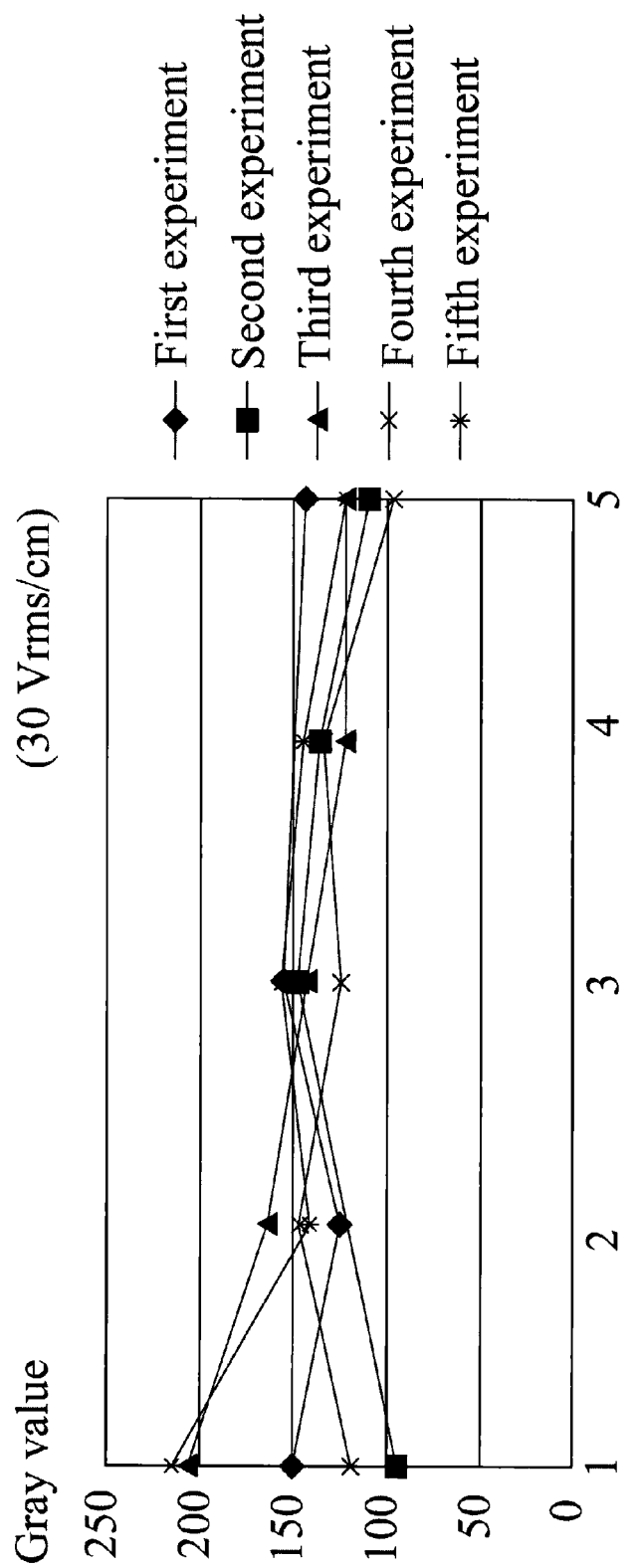
FIG. 4B is an illustration of chemilluminescence light reproducibility using a microfluidic mixing system with electric field according to a first embodiment of the present invention.

With reference to FIG. 4A for illustrating chemilluminescence reproducibility of using a microfluidic mixing system without electric field in accordance with a first embodiment of the invention is depicted. With reference to FIG. 4B for an illustrating chemilluminescence reproducibility of using a microfluidic mixing system with electric field in accordance with a first embodiment of the invention is depicted.

In the embodiment, the CCD is utilized to detect the chemiluminescence optical signals. Redox reagent such as hydrogen peroxide is firstly placed in the mixing cavity, and luminol and the catalyst (e.g. potassium ferricyanide) then are added to generate luminescence after reaction. Sucrose aqueous solution is utilized to mix with one of luminol, hydrogen peroxide or potassium ferricyanide to achieve the goal of simulating the blood viscosity.

After the experiments without electric field and with electric field are continuously performed for five times, software ACDSee 10.0 is utilized to cut all images into pictures. The picture with the greatest luminescence intensity by adding potassium ferricyanide is selected, and a square with the maximum area then is taken at the central containing cavity through Scion Image. An average gray value of its scope is read on, and the times of adding potassium ferricyanide in each experiment are taken for drawing. Accordingly, the drawing result is shown in FIG. 4A and FIG. 4B.

The drawings show that the reproducibility under a condition of applying electric filed is better than the reproducibility under a condition of not-applying electric field. The brightness is unstable when electric field is not applied. In another word, the advantages of shortening time and achieving higher reproducibility can be obtained when the electric field is added.

Figure 5:
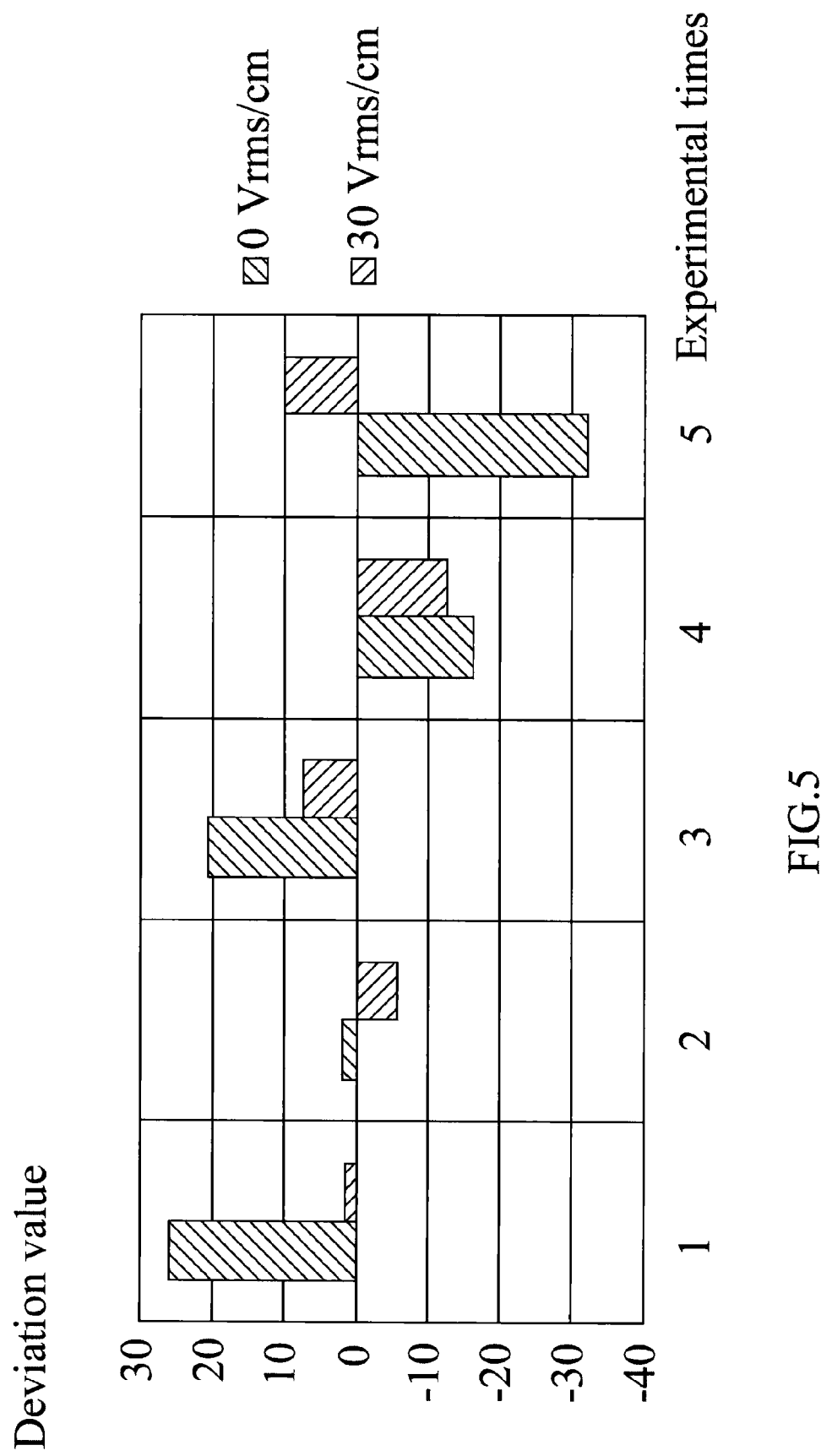
FIG. 5 is an illustration of a deviation value calculation of chemiluminescence optical signals according to a first embodiment.

With reference to FIG. 5 for a schematic diagram of a deviation value calculation of the chemiluminescence optical signals in accordance with a first embodiment is depicted. The deviation value calculation is that (experimental values−average values)/average values×100%. While imposing the electric field, AC induced electro-osmotic flow enhances the mixing efficiency of the catalyst, the redox reagent and the luminol, and the deviation value of the chemiluminescence optical signals is reduced to improve the reproducibility.

<A Second Embodiment: Taking the PMT for Detection>

Figure 6:
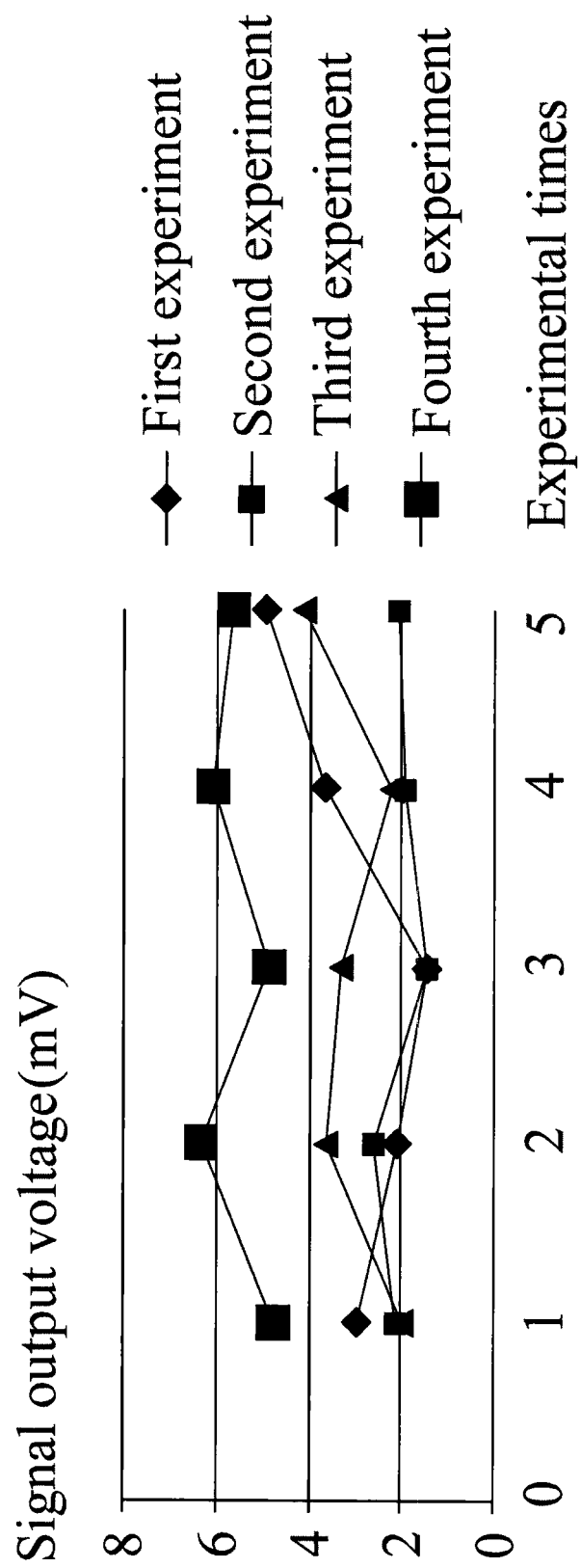
FIG. 6 is an illustration of a microfluidic mixing system according to a second embodiment of the present invention.
Figure 7:
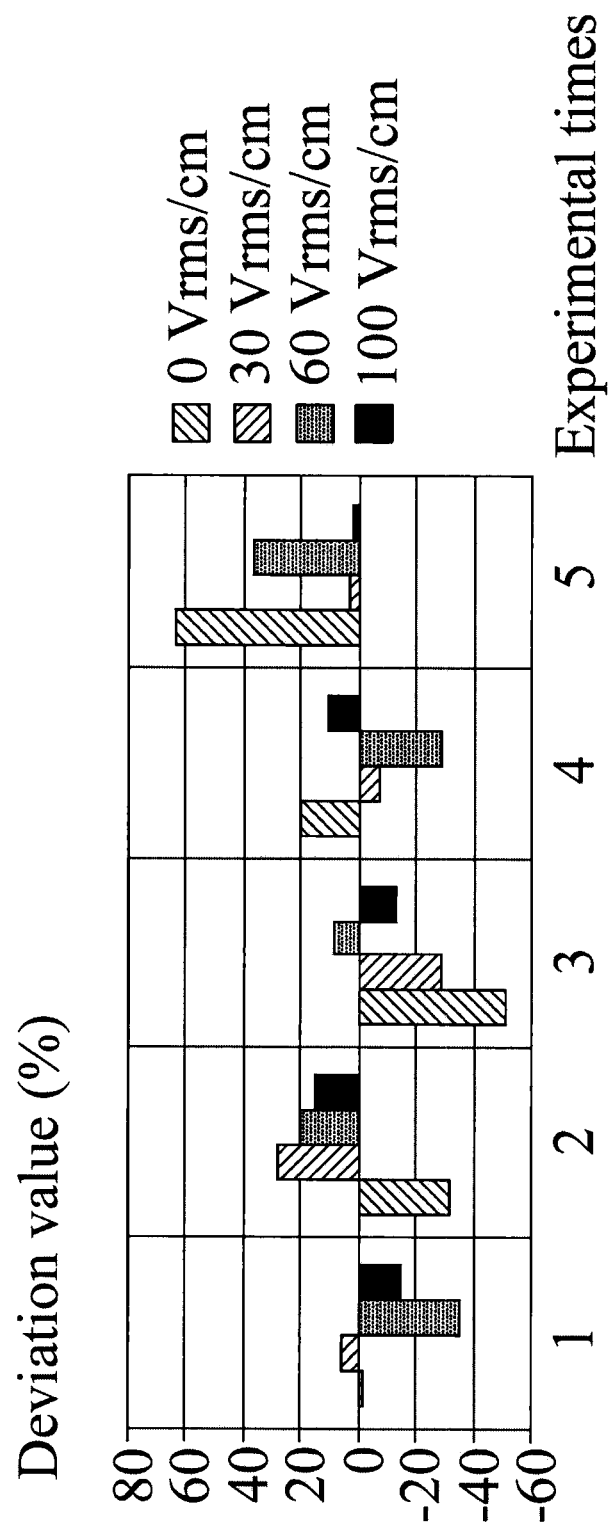
FIG. 7 is an illustration of a deviation value calculation of chemiluminescence optical signals according to a second embodiment.

With reference to FIG. 6 for a schematic diagram of a microfluidic mixing system in accordance with a second embodiment of the invention is depicted. With reference to FIG. 7 for a schematic diagram of a deviation value calculation of chemiluminescence optical signals in accordance with a second embodiment is depicted.

When the PMT is adopted to detect the chemiluminescence optical signals, the signals are easily determined and read. AC induced electro-osmotic flow enhances the mixing efficiency of the catalyst, the redox reagent and the luminol in a central micro-mixing cavity and improves the reproducibility of the chemiluminescence optical signals.

The invention utilizes sucrose aqueous solution to simulate the blood viscosity. The observation can be performed by chemical light emitting system and continuously injecting chemicals at fixed quantity. While imposing a high frequency alternating current electric field (100 kHz, 30V/cm) on a mixer, the mixing efficiency improved by non-linear electro-kinetic flow can be observed by using a highly sensitive black-white camera for acquiring luminescence, and the difference between the electric field that is not imposed and the high frequency alternating current electric filed that is imposed is also discussed.

The experiment result testified that when the electric field is not imposed, the solution within the central channel is influenced by viscosity so that the phenomenon of non-uniformly mixing the solution occurs. Alternatively, while imposing an alternating current electric field, the reagents in the mixing cavity can be rapidly and uniformly mixed in short time to obtain better signal reproducibility. By adjusting other experimental conditions, the rapid quantification for ferric ion concentration in blood can be achieved.

The mixer can be applied to the chemiluminescence experiment through the verification of the experiment and bioluminescence experiment. However, the luminescence intensity of bioluminescence is too weak. The foregoing concern must be observed by confocal focusing to prevent the periphery of luminescent place from being interfered with noise. Accordingly, if the mixer is combined with a confocal microscope and proper lens sets to achieve the optimum observation condition, and the quantitative analysis can also be applied with the foregoing facility.

The present invention improves over the prior art and complies with patent application requirements, and thus is duly filed for patent application. While the invention has been described by device of specific embodiments, numerous modifications and variations could be made thereto by those generally skilled in the art without departing from the scope and spirit of the invention set forth in the claims.

What is claimed is:

1. A microfluidic mixing chip having a light emitting compound, comprising:
    a first side cavity;
    a second side cavity; and
    a mixing cavity disposed between the first side cavity and the second side cavity and connected to the first side cavity and the second side cavity through microchannels, the mixing cavity being joined to the microchannels at sharp corners and having the light emitting compound, a redox reagent and a catalyst;
    wherein a pair of electrodes are disposed to the first side cavity and the second side cavity to provide a power source with only an identical phase of high frequency alternating current electric field to induce electric charges at the surfaces of the sharp corners to generate electro-osmotic flow, and the light emitting compound, the redox reagent and the catalyst are mixed in the mixing cavity by utilizing the power source with high frequency alternating current electric field, thereby producing a chemiluminescence optical signal or a bioluminescence optical signal.

2. The microfluidic mixing chip as recited in claim 1, wherein the light emitting compound comprises lucigenin, luminol or lophine.

3. The microfluidic mixing chip as recited in claim 1, wherein the redox reagent comprises hydrogen peroxide or oxygen.

4. The microfluidic mixing chip as recited in claim 1, wherein the mixing cavity further contains pH buffer, and the mixing cavity filled with the pH buffer mixes the catalyst, the light emitting compound and the redox reagent to generate the chemiluminescence optical signal or the bioluminescence optical signal.

5. A microfluidic mixing system having a light emitting compound, comprising:
- a microfluidic mixing chip comprising:
- a first side cavity;
- a second side cavity; and
- a mixing cavity disposed between the first side cavity and the second side cavity and connected to the first side cavity and the second side cavity through microchannels, the mixing cavity being joined to the microchannels at sharp corners and having the light emitting compound, a catalyst and a redox reagent;
- an electrode pair disposed to the first side cavity and the second side cavity respectively; and
- a power supplier for providing a power source with only an identical phase of high frequency alternating current electric field to induce electric charges at the surfaces of the sharp corners of the mixing cavity to generate electro-osmotic flow, wherein the light emitting compound, the redox reagent and the catalyst are mixed in the mixing cavity by utilizing the power source with high frequency alternating current electric field, thereby generating a chemiluminescence optical signal or a bioluminescence optical signal.

6. The microfluidic mixing system as recited in claim 5, wherein the light emitting compound comprises lucigenin, luminol or lophine.

7. The microfluidic mixing system as recited in claim 5, wherein the redox reagent comprises hydrogen peroxide or oxygen.

8. The microfluidic mixing system as recited in claim 5, wherein the mixing cavity further contains pH buffer, and the mixing cavity filled with the pH buffer mixes the catalyst, the light emitting compound and the redox reagent to generate the chemiluminescence optical signal or the bioluminescence optical signal.

9. The microfluidic mixing system as recited in claim 5, further comprising a voltage amplifier connected to the power supplier to amplify electric signal of the power source.

10. The microfluidic mixing system as recited in claim 5, further comprising a photon sensitive detector connected to the microfluidic mixing chip to detect the chemiluminescence optical signal or the bioluminescence optical signal.

11. The microfluidic mixing system as recited in claim 10, further comprising a focusing optics set connected to the photon sensitive detector to focus the chemiluminescence optical signal or the bioluminescence optical signal.

12. The microfluidic mixing system as recited in claim 10, wherein the photon sensitive detector is a charge coupled device (CCD), or a photo multiplier tube (PMT).

13. The microfluidic mixing system as recited in claim 5, wherein the electrode pair is a platinum electrode.

* * * * *